United States Patent
Nosanchuk et al.

(10) Patent No.: US 6,509,325 B1
(45) Date of Patent: Jan. 21, 2003

(54) METHOD FOR INHIBITING MELANOGENESIS AND USES THEREOF

(75) Inventors: Joshua D. Nosanchuk, Upper Saddle River, NJ (US); Arturo Casadevall, Pelham, NY (US); Rafael Ovalle, New York, NY (US)

(73) Assignee: Albert Einstein College of Medicine of Yeshiva University, Bronx, NY (US)

(*) Notice: Subject to any disclaimer, the term of this patent is extended or adjusted under 35 U.S.C. 154(b) by 0 days.

(21) Appl. No.: 09/563,791

(22) Filed: May 2, 2000

(51) Int. Cl.$^7$ .......................... A61P 31/10; A61K 9/08; A61K 31/662; A61K 31/198
(52) U.S. Cl. ...................... 514/109; 514/114; 514/561; 424/423; 424/422
(58) Field of Search .................... 514/76, 109, 114, 514/561; 424/423, 405, 422

(56) References Cited

U.S. PATENT DOCUMENTS 5,656,515 A * 8/1997 Camden .................... 514/76

OTHER PUBLICATIONS

Butler and Day, Fungal melanins: a review. Can. J. Microbiol., 44(12):1115–36, Dec. 1998.

Doering et al., Melanin as a potential crypotococcal defence against microbicidal proteins. Med. Mycol., 37(3):175–81, Jun. 1999.

Nosanchuk et al., Melanization of Crptococcus neoformans in murine infection. Mol. Cell. Biol., 19(1):745–50, Jan. 1999.

Nosanchuk and Casadevall, Glyphosate inhibits melanization of Cryptococcus neoformans and affects survival following systemic infection in mice. Abstract of the 99th General Meeting of the American Society for Microbiology, Abstract F–49, 1999.

Rosas et al., Synthesis of polymerized melanin by Cryptococcus neoformans in infected rodents. Infect. Immun., 68(5):2845–53, May 2000.

Salas et al., Effect of the laccase gene, CNLAC1, on virulence of Cryptococcus neoformans. J. Exp. Med., 184(2):377–86, Aug. 1, 1996.

Wang et al., Cryptococcus neoformans melanin and virulence: mechanism of action. Infect. Immun., 63(8):3131–36, Aug. 1995.

Wang and Casadevall, Growth of Crytococcus neoformans in presence of L–dopa decreases its susceptibility to amphotericin B. Antimicrob. Chemother., 38(11):2648–50, Nov. 1994.

* cited by examiner

*Primary Examiner*—Edward J. Webman
*Assistant Examiner*—Helen Nguyen
(74) *Attorney, Agent, or Firm*—Amster, Rothstein & Ebenstein

(57) ABSTRACT

The present invention provides a method for treating a subject infected with a mammalian pathogenic fungus which uses melanin in virulence, by administering to the subject an amount of glyphosate effective to treat the infection. The present invention further provides a method for inhibiting proliferation of a mammalian pathogenic fungus which uses melanin in virulence, by contacting the fungus with an amount of glyphosate effective to inhibit the proliferation of the fungus. Additionally, the present invention further provides a method for inhibiting melanogenesis in a microorganism which produces melanin, by contacting the microorganism with an amount of glyphosate effective to inhibit melanogenesis in the microorganism.

10 Claims, 4 Drawing Sheets

METHOD FOR INHIBITING MELANOGENESIS AND USES THEREOF

STATEMENT OF GOVERNMENT INTEREST

This invention was made with government support under NIH Grant No. KO8-AIO1489. As such, the United States government has certain rights in this invention.

BACKGROUND OF THE INVENTION

Systemic fungal diseases in humans, arising through fungal infections, may be chronic and even life-threatening. Many of the causative fungi which produce systemic mycoses in humans are opportunists: they are not usually pathogenic unless they enter a compromised host. Opportunistic fungal infections frequently occur in patients with acquired immune deficiency syndrome (AIDS), azotemia, bronchiectasis, bums, diabetes mellitus, emphysema, leukemia, lymphoma, or tuberculosis. Systemic mycoses affecting severely immunocompromised patients often result in rapidly progressive pneumonia, fungemia, or manifestations of extrapulmonary dissemination. Moreover, in immunocompetent patients, systemic mycoses typically have a chronic course. Amphotericin B remains the standard therapy for most life-threatening systemic mycoses, even though it is highly toxic and can result in impairment of renal functional [35].

Cryptococcosis, a typical opportunistic infection caused by the human pathogenic fungus *Cryptococcus neoformans*, frequently leads to chronic, life-threatening meningitis, but may also disseminate to the bones, skin, viscera, and other sites [35]. *Cryptococcus neoformans* is primarily a pathogen for immunocompromised individuals. In patients with impaired immune systems, cryptococcal meningitis is often incurable because existing antifungal agents are unable to eradicate the infection. *Cryptococcus neoformans* is a defining opportunistic pathogen in patients with AIDS, although patients with Hodgkin's or other lymphomas or sarcoidosis, or those receiving long-term corticosteroid therapy, are also at increased risk [35]. In the United States and Europe, *C. neoformans* causes meningoencephalitis, a life-threatening meningitis, in 5–10% of patients with AIDS [1, 2]. The incidence of cryptococcosis is significantly higher in sub-Saharan Africa [2] and Southeast Asia [3].

Although most cryptococcal infections have a self-limited, subacute, or chronic course, AIDS-associated cryptococcal infection may present with severe, progressive meningoencephalitis [35]. Patients with advanced human immunodeficiency virus (HIV) infection frequently relapse, despite successful initial treatment of cryptococcosis with antifungal agents [4, 5]. As a consequence, cryptococcosis in the setting of AIDS is currently considered incurable [6]. For meningitis in non-AIDS patients, the standard regimen is 6 weeks of 0.3 mg/kg/day of amphotericin B intravenously, combined with 100 to 150 mg/day of flucytosine. Renal and hematologic function must be evaluated before and regularly during therapy. AIDS patients more often have suboptimal therapeutic responses. Amphotericin B and flucytosine are recommended as initial treatment in AIDS patients, at least for two weeks. Oral fluconazole (200 to 400 mg/day) can be used thereafter. Most cases relapse if treatment is stopped, so chronic suppressive therapy is needed [35].

One of the important virulence factors in *C. neoformans* is its ability to synthesize melanin during infection [7, 8, 24, 25]. Melanins are amorphous, insoluble pigments that are stable free radicals; they also manifest distinct electron-spin resonance spectral features [9, 10]. Melanins are found in diverse species in all biological kingdoms, and have been associated with camouflage, drug binding, sexual display, and the absorption and dissipation of various forms of energy [11]. Melanin synthesis is a widespread phenomenon among microorganisms, including several important human and plant pathogens. Several pathogenic fungi, such as *Aspergillus fumigatus* and *Histoplasma capsulatum*, synthesize melanin. Among the plant pathogenic fungi, melanin synthesis appears to be necessary for cellular invasion [44]. Several bacteria, including *Mycobacterium leprae*, also make melanin pigments.

In *C. neoformans*, melanin appears to function in virulence by protecting the fungus against the host's immune system [14, 15]. Specifically, melanin has been shown to protect the fungus against oxidants [12, 13], defensins and protegrins [15], and macrophages in vitro [16], as well as extremes in temperature [17]. Additionally, melanogenesis has been shown to reduce the susceptibility of *C. neoformans* to amphotericin B, the primary antifungal drug [13, 14]. Melanized cryptococcal cells interfere with the development of a protective T-cell response in mice [18]. In addition, melanin-deficient mutants are avirulent in murine infections [19]. Currently, there are no compounds that are known to inhibit melanogenesis in *C. neoformans*.

The prognosis for AIDS patients with cryptococcal disease continues to be extremely poor [40]. One development in the treatment of cryptococcosis is a monoclonal antibody against the major polysaccharide in the capsule of *C. neoformans*. This antibody is currently being evaluated for phase I clinical trials in the treatment of AIDS patients infected with *C. neoformans* [41]. Nevertheless, with growing numbers of immunocompromised individuals worldwide, further advances in the management of this disease are desperately needed.

Glyphosate (N-phosphonomethylglycine) is a synthetic crystalline amino acid with an empirical formula of $C_3H_8NO_5P$. The compound, which is relatively nontoxic to humans, is used worldwide as a broad-spectrum systemic herbicide [28, 29], and is marketed as "Roundup" (Monsanto Company) in. the United States. Glyphosate inhibits synthesis of aromatic amino acids via the shikimate pathway. In particular, glyphosate is known to inhibit polymer formation in plants by blocking the metabolism of phenolic compounds [24, 25].

In addition to a herbicidal effect on plants, glyphosate inhibits many microorganisms. Recently, glyphosate was shown to inhibit the in vitro growth of several parasitic species of the phylum Apicomplexan [31]. Glyphosate has also been shown to inhibit growth of diverse fungal species, particularly those which are pathogenic to plants [33, 46, 47]. However, prior to the present invention, it was not known that glyphosate could inhibit melanogenesis in, and proliferation of, mammalian pathogenic fungi which use melanin in virulence.

SUMMARY OF THE INVENTION

The present invention is based on the discovery that glyphosate inhibits both melanogenesis in *Cryptococcus neoformans* and growth and proliferation of *Cryptococcus neoformans*. This discovery will have implications in the treatment of infections, such as cryptococcosis, where the infectious microorganism is one which uses melanin in virulence. In particular, this finding will have important implications in the treatment of AIDS patients who are infected with *Cryptococcus neoformans*.

Accordingly, the present invention provides a method for treating a subject infected with a mammalian pathogenic fungus which uses melanin in virulence, by administering to the subject an amount of glyphosate effective to treat the infection. The present invention further provides a method for inhibiting proliferation of a mammalian pathogenic fungus which uses melanin in virulence, by contacting the fungus with an amount of glyphosate effective to inhibit the proliferation of the fungus. Finally, the present invention further provides a method for inhibiting melanogenesis in a microorganism which produces melanin, by contacting the microorganism with an amount of glyphosate effective to inhibit melanogenesis in the microorganism.

Additional objects of the present invention will be apparent in view of the description which follows.

DETAILED DESCRIPTION OF THE INVENTION

Figure 1:
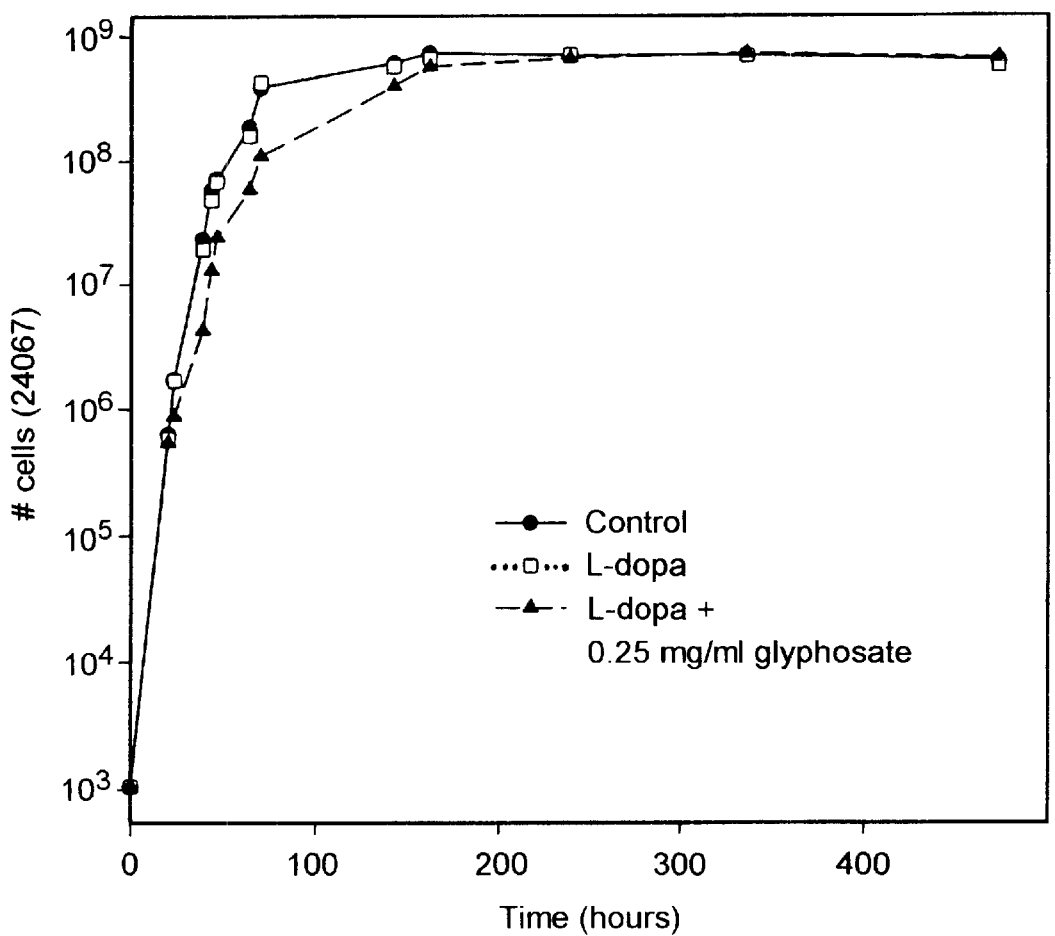
FIG. 1 depicts the growth curves of *C. neoformans* strain 24067 in minimal media: without L-dopa (control), with 1 mM L-dopa, and with 1 mM L-dopa and 250 µg/ml glyphosate.

The present invention provides a method for treating a subject infected with a mammalian pathogenic fungus which uses melanin in virulence. As used herein, a "subject" is a mammal, including, without limitation, a cow, dog, human, monkey, mouse, pig, or rat, but is preferably a human. As further used herein, a "mammalian pathogenic fungus which uses melanin in virulence" means any fungus that causes or produces disease in a mammal and for which melanin is one of its virulence factors. Where a fungus uses melanin in virulence, melanin may, for example, be associated with protection against environmental factors, e.g., camouflage, drug binding, reduced susceptibility to drugs, sexual display, the absorption and dissipation of various forms of energy, and the like. Additionally, where a fungus uses melanin in virulence, melanin may, for example, be associated with protection against a host's immune system. For example, melanin may be involved in protecting the fungus against oxidants, defensins and protegrins, macrophages, extremes in temperature [17], and development of a protective T-cell response [35]. Examples of mammalian pathogenic fungi which use melanin in virulence include, without limitation, *Ajellomyces dermatitidis, Aspergillus fumigatus, Aspergillus niger, Blastomyces dermatitidis, Cryptococcus neoformans, Histoplasma capsulatum, Sporothrix shenckii,* and *Wangiella dermatitidis*. In the method of the present invention, however, the mammalian pathogenic fungus which uses melanin in virulence is preferably *Cryptococcus neoformans*.

The method of the present invention comprises administering to a subject infected with a mammalian pathogenic fungus which uses melanin in virulence an amount of glyphosate. As used herein, "glyphosate" refers to N-phosphonomethylglycine (both the free amino acid and its salts) and analogues thereof, including, for example, a functional variant of glyphosate which has glyphosate biological activity. As further used herein, the term "glyphosate biological activity" refers to glyphosate activity which inhibits melanogenesis in a mammalian pathogenic fungus which uses melanin in virulence. Preferably, glyphosate is administered to a subject who has acquired immune deficiency syndrome (AIDS) and who is also infected with *Cryptococcus neoformans*.

In the method of the present invention, glyphosate is administered to a subject infected with a mammalian pathogenic fungus which uses melanin in virulence in an amount which is effective to treat the infection. As used herein, the phrase "effective to treat the infection" means effective to ameliorate or minimize the clinical impairment or symptoms resulting from infection with a mammalian pathogenic fungus which uses melanin in virulence. For example, where the subject is infected with *Cryptococcus neoformans*, the amount of glyphosate effective to treat the infection is that which can ameliorate or minimize the symptoms of cryptococcosis, including, without limitation, basal cell carcinoma; cryptococcal meningitis; cutaneous lesions; cystic masses of yeasts in involved tissues, such as the kidneys, liver, prostate, and spleen; focal lesions of the abdominal viscera, bone, brain, lungs, and skin; progressive pneumonia; pulmonary infection; and subcutaneous nodules. The amount of glyphosate effective to treat an infection in a subject infected with a mammalian pathogenic fungus which uses melanin in virulence will vary depending on the particular factors of each case, including the patient's weight and the severity of the patient's condition. Nevertheless, the appropriate amount of glyphosate can be readily determined by the skilled artisan.

In the method of the present invention, glyphosate may be administered to a human or animal subject by known procedures, including, without limitation, oral administration and parenteral administration, e.g., by intradermal, intramuscular, intraperitoneal, intravenous, or subcutaneous injection. Preferably, the glyphosate is administered intraperitoneally. For oral administration, a formulation of glyphosate may be presented as capsules, tablets, powders, granules, or as a suspension. The formulation may have conventional additives, such as lactose, mannitol, corn starch, or potato starch. The formulation may also be presented with binders, such as crystalline cellulose, cellulose derivatives, acacia, corn starch, or gelatins. Additionally, the formulation may be presented with disintegrators, such as corn starch, potato starch, or sodium carboxymethyl-cellulose. The formulation may also be presented with dibasic calcium phosphate anhydrous or sodium starch glycolate. Finally, the formulation may be presented with lubricants, such as talc or magnesium stearate.

For injection, glyphosate may be combined with a sterile aqueous solution which is preferably isotonic with the blood of the subject. Such a formulation may be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulations may be present in unit or multi-dose containers, such as sealed ampules or vials.

It is also within the confines of the present invention that glyphosate be administered to a subject infected with a mammalian pathogenic fungus which uses melanin in virulence, either alone or in combination with one or more antimicrobial drugs. Examples of antimicrobial drugs with which glyphosate may be combined include, without limitation, amphotericin B, fluconazole, flucytosine, itraconazole, and ketoconazole. It is envisaged that the ability of glyphosate to inhibit melanogenesis may enhance the therapeutic efficacy of other antimicrobial drugs by improving their penetration into microbial cells.

The inhibition of melanogenesis is a novel antimicrobial strategy against mammalian pathogenic fungi which synthesize melanins during infection. Accordingly, the present invention further provides a method for inhibiting proliferation of a mammalian pathogenic fungus which uses melanin in virulence. As used herein, "proliferation" includes, without limitation, growth, multiplication, replication, and reproduction of a fungus. The method of the present invention comprises contacting the mammalian pathogenic fungus with an amount of glyphosate effective to inhibit the proliferation of the fungus. As described above, examples of mammalian pathogenic fungi which use melanin in virulence include, without limitation, *Ajellomyces dermatitidis*, *Aspergillus fumigatus*, *Aspergillus niger*, *Blastomyces dermatitidis*, *Cryptococcus neoformans*, *Histoplasma capsulatum*, *Sporothrix shenckii*, and *Wangiella dermatitidis*. In the method of the present invention, the mammalian pathogenic fungus which uses melanin in virulence is preferably *Cryptococcus neoformans*.

According to the method of the present invention, a mammalian pathogenic fungus which uses melanin in virulence may be contacted, either in vitro or in vivo, with glyphosate. When in vivo, contacting between the fungus and the glyphosate may be effected by any of the above-described methods of administering glyphosate to a subject (e.g., oral or parenteral). When in vitro, a culture of the fungus may, for example, be incubated with a preparation containing glyphosate. The glyphosate's effect on proliferation of the fungus may be assessed by any of the methods known in the art, including visual assays for turbidity of plates containing fungus suspensions.

The present invention also provides a method for inhibiting melanogenesis in a microorganism which produces melanin. As used herein, "melanogenesis" means the production of melanin. The method of the present invention comprises contacting a microorganism which produces melanin with an amount of glyphosate effective to inhibit melanogenesis in the microorganism. The microorganism of the present invention may be any bacterium, fungus, protozoan, yeast, or other microorganism that produces melanin. Examples include, without limitation, and *Ajellomyces dermatitidis*, *Alternaria alternata*, *Aspergillus fumigatus*, *Aspergillus nidulans*, *Blastomyces dermatitidis*, *Burkholderia cepacia*, *Colletotrichum lagena*, *Cryptococcus neoformans*, *Gaeumannomyces graminis*, *Histoplasma capsulatum*, *Pseudomonas tolaasii*, *Sporothrix shenckii*, and *Wangiella dermatitidis*. Preferably, the microorganism which produces melanin is *Cryptococcus neoformans*. In the method of the present invention, the microorganism which produces melanin may be contacted, either in vitro or in vivo, with glyphosate. When in vivo, contacting between the microorganism and the glyphosate may be effected by any of the above-described methods of administering glyphosate to a subject (e.g., oral or parenteral). When in vitro, a culture of the microorganism may, for example, be incubated with a preparation containing glyphosate, and melanogenesis of the microorganism may be assessed visually.

The present invention is described in the following Experimental Details section, which is set forth to aid in the understanding of the invention, and should not be construed to limit in any way the scope of the invention as defined in the claims which follow thereafter.

EXPERIMENTAL DETAILS

1. Introduction

Fungal pathogens are notorious for causing chronic and latent infections, but the mechanism by which they evade the immune response is poorly understood. The ability of *C. neoformans* to produce melanin is associated with virulence, but the specific role of melanin in the pathogenesis of infection is not clear. It is known that *C. neoformans* synthesizes melanin in the presence of phenolic precursors like L-Dopa. Through autopolymerization [21], the fungus oxidizes the phenolic compounds to quinone intermediates which form an electron-dense layer in the cell wall [20]. Intermediate forms in the melanin-synthesis pathway of *C. neoformans* have not been completely determined, and the exact structure of the melanin is unknown [22, 23]. It is known, however, that *C. neoformans* is melanized in the environment [24]. Furthermore, melanogenesis of *C. neoformans* occurs during infection in rodents [25, 26] and in humans [27].

Glyphosate's primary mechanism of action is inhibition of the shikimate-pathway enzyme, 5-enolpyruvylshikimate 3-phosphate synthase (EPSPS) [30, 31]. The shikimate pathway is essential for the formation of aromatic amino acids. Since this pathway is absent in humans who depend on exogenous sources for folates, there is a low risk for toxicity; thus, glyphosate is designated by the Environmental Protection Agency as a Category E herbicide ("evidence of noncarcinogenicity for humans") [28].

Since *C. neoformans* grows in a defined chemical media consisting of glucose, $MgSO_4$, $KH_2PO_4$, glycine, and thiamine [37], it is able to synthesize its own amino acids. The *Saccaromyces cerivisiae* genome contains a multifunctional arom complex, consisting of a pentafunctional polypeptide that catalyzes the first five steps of the shikimate pathway, ending at EPSPS [38]. The ARO 2 gene, which encodes chorismate synthase in *S. cerivisiae*, has been characterized [39]. The inventors hypothesized that *C. neoformans* similarly utilizes the shikimic acid pathway, and that, therefore, glyphosate would inhibit the growth of *C. neoformans*. Because cryptococcal cells-require phenolic compounds to synthesize melanin, it was further hypothesized that glyphosate could affect melanization. The formation of melanin in *C. neoformans* in culture can readily be detected upon visual examination [11], thereby providing a simple method for studying the effects of glyphosate on melanization.

2. Materials and Methods

A. Glyphosate Inhibition of *C. neoformans*

*Cryptococcus neoformans* serotype D strain 24067 was obtained from the American Type Culture Collection (Rockville, Md.), and grown overnight at 30° C. with shaking in Sabouraud dextrose media (Sab) obtained from Difco Laboratories (Detroit, Mich.). Cells were collected and washed three times with phosphate-buffered saline (PBS: 0.137 M NaCl and 0.003 M sodium phosphate; pH 7.4). A suspension of 250 organisms per 1 ml of Sab was made. Glyphosate was obtained from the Sigma Chemical Co. (St. Louis, Mo.). Polystyrene 96-well plates (Corning Glass Works, Corning, N.Y.) were used to test 100-$\mu$l aliquots of the *C. neoformans* suspension with different concentrations of glyphosate. Each concentration was tested in triplicate. The plates were incubated at 30° C., and growth was assayed visually for turbidity after 72 h.

B. Effect on Melanization of Sub-Inhibitory Concentrations of Glyphosate

*Cryptococcus neoformans* cultures were grown at 30° C. in a defined chemical medium (15 mM glucose, 10 mM $MgSO_4$, 29.4 mM $KH_2PO_4$, 13 mM glycine, and 3 μM thiamine) and 1 mM L-dopa (Sigma), in the presence of sub-inhibitory concentrations of glyphosate. Positive melanin controls were cultures containing L-dopa without glyphosate; negative controls were cultures lacking both L-dopa and glyphosate. All cultures were grown in duplicate. The cultures were examined visually for melanization. The growth rate of the cells in each culture was determined by counting, with a hemocytometer, the number of cells per ml at various times after the initiation of the culture.

C. Effect of Glyphosate on L-dopa Autopolymerization and on *C. neoformans* Laccase In solution, L-dopa slowly autopolymerizes to form melanin [20]. To determine if glyphosate interferes with this process, 30-ml solutions of 1 mM L-dopa, containing serially-diluted concentrations of glyphosate, were prepared in culture flasks. The samples were left on the benchtop at room temperature. An Ultraspec 2000 spectrophotometer (Pharmacia Biotech, Cambridge, England) was used to assess absorption at 270λ after 3 days and 20 days. The spectrophotometer was calibrated using the sample containing 1 mM L-dopa and 2 mg/ml of glyphosate. A freshly-prepared solution of the same concentrations was tested for comparison. The positive control was a solution of 1 mM L-dopa without glyphosate.

The ability of glyphosate to inhibit the activity of *C. neoformans* laccase was assessed by a modification of a previously-described phenol oxidase assay [44]. Briefly, *C. neoformans* strain 24067 was grown overnight in Sab at 30° C. Cells were washed in PBS, then 0.1 ml of cells were incubated, at 30° C. for 2h, with 0.1 ml of 10 mM L-epinephrine and varying concentrations of glyphosate in 0.8 ml of PBS. The positive control was a solution without glyphosate. The reaction was terminated by the addition of 10 μl of 1 M KCN. The samples were centrifuged, then the solutions were assayed by spectrophotometer at 480λ. The spectrophotometer was calibrated using a freshly-prepared sample consisting of 0.8 ml of PBS, 0.1 ml of *C. neoformans*, and 0.1 ml of 10 mM l-epinephrine.

D. Effect of Glyphosate on Experimental *C. neoformans* Infection

*Cryptococcus neoformans* cells were collected as described above. BALB/c mice (National Cancer Institute (NCI), Bethesda, Md.), 6–8 weeks old, were injected intravenously (i.v.) by the tail veins with 1×10⁶ organisms. Either glyphosate (experiment A: 0.75 mg in 0.1 ml of $dH_2O$; experiment B: 1.5 mg in 0.2 ml of $dH_2O$) or PBS was injected intraperitoneally (i.p.) at 24, 48, and 72 h after infection. In experiment A, uninfected control mice were injected with glyphosate at the same time intervals. A/J Cr mice (NCI, Bethesda, Md.) were also studied using i.v. infection with 5×10⁵ organisms and i.p. injection of 1 mg of glyphosate at the same time intervals. Forty-four days after infection, the A/J Cr mice were killed, and the lungs were isolated and homogenized in 5 ml of PBS. 100 μl of ¹⁄₁₀₀ and ¹⁄₁₀₀₀ dilutions of the homogenates in PBS were then plated on Sab agar. Colony-forming units (CFUs) were determined after incubation of the plates at 30° C. for 48 h (1 colony=1 CFU). BALB/c mice were also injected i.v. with 1×10⁶ organisms and i.p. with 1.5 mg of glyphosate daily for the first three days, followed by 0.75 mg of glyphosate three times a week for one month. Control mice were injected with PBS instead of glyphosate.

E. Effect on the Isolation of Melanin "Ghosts" from Infected Tissue in Mice

BALB/c mice were infected i.v. with 1×10⁶ organisms, and injected i.p. with 1.5 mg of glyphosate or PBS at 24, 48, and 72 h after infection. Three days after infection, 2 mice from each group were killed, and their lungs and brains were collected. Three mice from each group were treated similarly at seven days after infection. The lungs were combined within each group, homogenized, then treated with denaturant, enzymes, and boiling HCl, as described [23]. The brains were similarly treated. Scanning electron microscopy was performed on the remaining debris, as described [23].

3. Statistics

Data analysis was performed using SPSS version 8. Student's T-test and Kaplan-Meier survival analysis were utilized.

4. Results

A. Growth Inhibition

To determine whether glyphosate affects the growth of *C. neoformans*, the fungus was cultured in the presence of different concentrations of glyphosate. After 72 h of incubation, growth inhibition was observed at concentrations >250 μg/ml of glyphosate, while no growth inhibition was observed at concentrations <250 μg/ml of glyphosate.

B. Inhibition of Melanization

Figure 2:
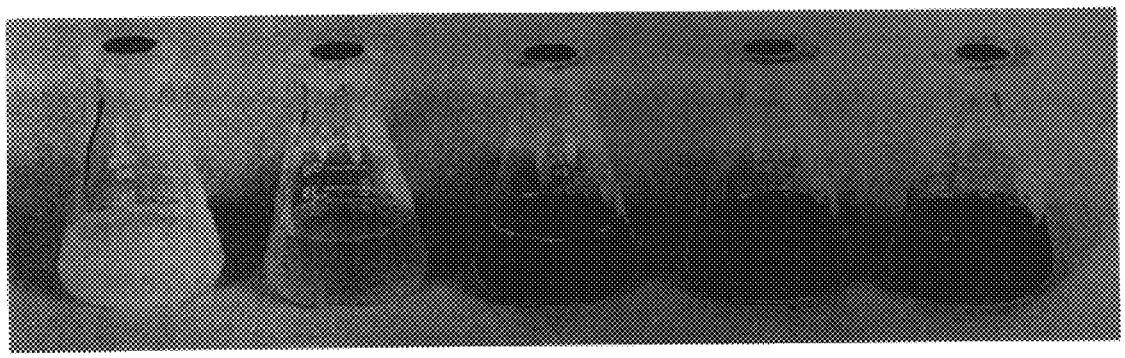
FIG. 2 illustrates results obtained when *C. neoformans* was grown for 10 days in minimal media with different concentrations of L-dopa and glyphosate. The cultures with 1 mM L-dopa and either 0 or 62.5 µg/ml glyphosate were heavily melanized.

Melanization was delayed in cultures with concentrations between 62.5 and 250 μg/ml of glyphosate. Growth curves (FIG. 1) and time of melanization (Table 1) for different concentrations of glyphosate are shown. FIG. 2 demonstrates the melanization state of cultures of *C. neoformans* incubated with various concentrations of glyphosate at day 10 of growth.

TABLE 1

| The concentration of glyphosate affects the rate of melanization in *C. neoformans*. | |
|---|---|
| Concentration of Glyphosate (μg/ml) | Melanization (day) |
| 0 | 7 |
| 62.5 | 10 |
| 125 | 13 |
| 250 | 15 |

C. Autopolymerization of L-dopa

Figure 3:
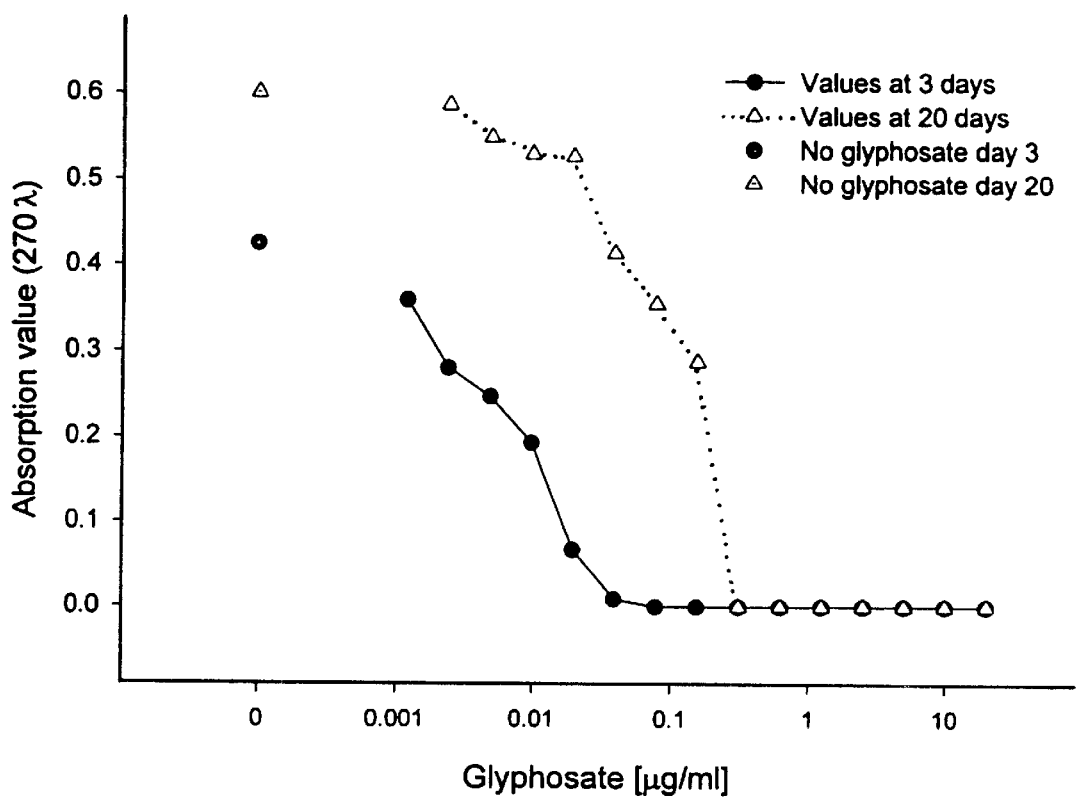
FIG. 3 sets out absorption measurements of the autopolymerization of L-dopa to melanin, with and without different concentrations of glyphosate. Measurements were obtained at a wavelength of 270λ using spectrophotometry.

Autopolymerization of L-dopa can be inhibited by glyphosate. At day 3, an absorption signal could be detected at concentrations of 39 μg/ml of glyphosate (FIG. 3). Solutions with concentrations as low as 0.12 μg/ml of glyphosate had lower absorption values than control solutions without the compound (0.359 vs. 0.425). At day 20, concentrations ≧31.3 μg/ml of glyphosate continued to inhibit melanin formation (FIG. 3). Absorption of the freshly-prepared solutions of 1 mM L-dopa with 2 mg/ml glyphosate were identical to the calibration values.

D. Survival

Figure 4:
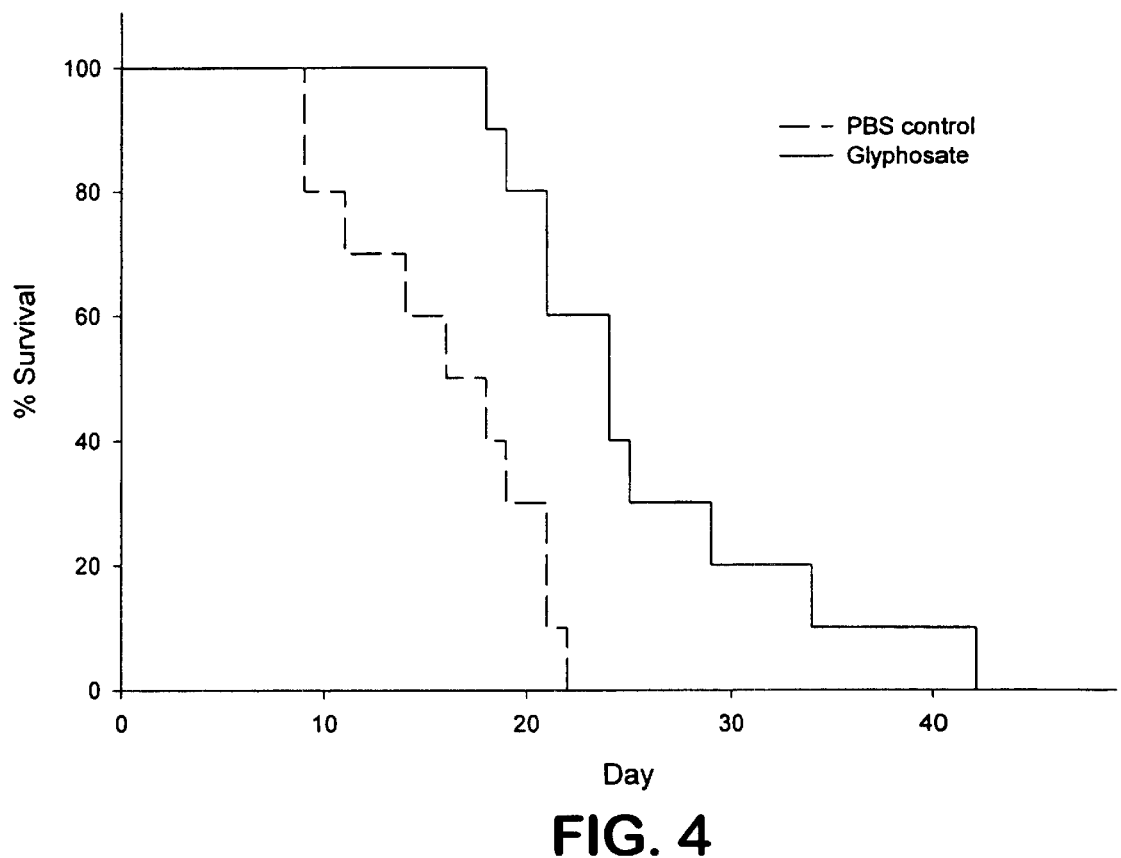
FIG. 4 depicts the survival of BALB/c mice which had been given 1.5 mg of glyphosate or PBS (control) intraperitoneally (i.p.) for three days following i.p. infection with $1\times10_6$ *C. neoformans* strain 24067.

Intraperitoneal administration of glyphosate to mice infected with *C. neoformans* significantly affected survival. Mean survival time and standard deviation by Kaplan-Meier analysis of BALB/c mice treated with 1.5 mg/day of glyphosate for three days was 25.7±2.36 days, compared to 15.9±1.57 days for the control mice (p=0.001) (FIG. 4). Mean survival was also significantly improved in the group treated with the 0.75 mg/day protocol (26.8±3.55 days vs.

20.4±1.31 days; p=0.049). Log$_{10}$ CFUs were determined from the lung homogenates of A/J Cr mice treated with or without glyphosate (n=13 in both groups). Log$_{10}$ CFUs in the glyphosate-treated group were significantly less than controls (8.62±1.12 vs. 9.63±0.21; p=0.004, T-test). Infected BALB/c mice were also treated orally with glyphosate by administering ad lib water containing the compound at concentrations of either 2 mg/ml or 10 mg/ml. However, no survival advantage was determined.

Discussion

Glyphosate is a compound used worldwide as a systemic herbicide. However, glyphosate also inhibits the growth of diverse microbial species. The inventors have demonstrated that glyphosate can inhibit growth and delay melanogenesis of *C. neoformans*. In vivo experiments show that glyphosate has therapeutic effects in mice infected with *C. neoformans*. Inhibition of *C. neoformans* replication is likely due to effects on the shikimate pathway's synthesis of essential folate precursors. Indeed, glyphosate and other compounds that disrupt the shikimate pathway [42, 43] may be useful therapeutics in the treatment of *C. neoformans* and other microorganisms. The mechanism of inhibition of melanogenesis is less certain. The observation that glyphosate interferes with the auto-oxidation of L-dopa may suggest that the compound directly inhibits melanin polymerization. Glyphosate can chelate several metal ions [37, 38, 39]; thus, it may directly interact with L-dopa or with highly-charged quinone intermediates of melanin. Additionally, glyphosate may also inhibit melanogenesis by inhibiting the activity of *C. neoformans* laccase.

References

1. Currie and Casadevall, Estimation of the prevalence of cryptococcal infection among HIV infected individuals in New York City. *Clin. Infect. Dis.*, 19:1029–33, 1994.
2. Mitchell and Perfect, Cryptococcus in the era of AIDS—100 years after the discovery of *Cryptococcus neoformans. Clinical Microbiology Reviews*, 8:515–48, 1995.
3. Spitzer et al., Persistence of the initial infection in recurrent cryptococcal meningitis. *Lancet*, 341:595–96, 1993.
4. Zuger et al., Cryptococcal disease in patients with the acquired immunodeficiency syndrome: diagnostic features and outcome of treatment. *Ann. Intern. Med.*, 104:234–40, 1986.
5. Dismukes, W. E., Management of cryptococcosis. *Clin. Infect. Dis.*, 17 (Suppl. 2):507–12, 1993.
6. Rhodes et al., Phenoloxidase activity and virulence in isogenic strains of *Cryptococcus neoformans. Infect. Immun.*, 36:1175–84, 1982.
7. Salas et al., Effect of the laccase gene, CNLAC1, on virulence of *Cryptococcus neoformans. J. Exp. Med.*, 184:377–86, 1996.
8. Enochs et al., A standardized test for the identification and characterization of melanins using electron paramagnetic (EPR) spectroscopy. *Pigment Cell Res.*, 6:91–99, 1993.
9. Sealy, R. C., Free radicals in melanin formation, structure and reactions. In: Armstrong et al., eds., *Free Radicals in Molecular Biology: Aging and Disease* (New York: Raven Press, 1984) 67–76.
10. Hill, Z. H., The function of melanin or six blind people examine an elephant. *BioEssays*, 14:49–56, 1992.
11. Wang and Casadevall, Susceptibility of melanized and nonmelanized *Cryptococcus neoformans* to nitrogen- and oxygen-derived oxidants. *Infection* and *Immunity*, 62(7): 3004–07, 1994.
12. Jacobson and Tinnell, Antioxidant function of fungal melanin. *J. Bacteriol.*, 175:7102–04, 1993.
13. Wang and Casadevall, Growth of *Cryptococcus neoformans* in presence of L-dopa decreases its susceptibility to amphotericin *B. Antimicrob. Agents Chemother.*, 38(11): 2648–50, 1994.
14. Doering et al., Melanin as a potential cryptococcal defense against microbicidal proteins. *Medical Mycology*, 37(3):175–82, 1999.
15. Wang et al., *Cryptococcus neoformans* melanin and virulence: mechanism of action. *Infect. Immun.*, 63:3131–36, 1995.
16. Rosas and Casadevall, Melanization affects susceptibility of *Cryptococcus neoformans* to heat and cold. *FEMS Microbiol. Lett.*, 153:265–72, 1997.
17. Huffnagle et al., Down-regulation of the afferent phase of T cell-mediated pulmonary inflammation and immunity by a high melanin-producing strain of *Cryptococcus neoformans. J. Immunol.*, 155:3507–16, 1995.
18. Kwon-Chung et al., Melanin-lacking mutants of *Cryptococcus neoformans* and their virulence for mice. *J. Bacteriol.*, 150(3):1414–21, 1982.
19. Wang and Casadevall, Melanin, melanin "ghosts," and melanin composition in *Cryptococcus neoformans. Infect. Immun.*, 64:2420–24, 1996.
20. Mason, H. S., Comparative biochemistry of the phenolase complex. *Advances in Enzymology*, 16:105–84, 1955.
21. Wheeler and Bell, Melanins and their importance in pathogenic fungi. *Current Topics Med. Mycol.*, 2:338–87, 1988.
22. Chedekel et al., Melanin standard method: empirical formula 2. *Pigment Cell Res.*, 5:240–46, 1992.
23. Nosanchuk et al., Evidence that *Cryptococcus neoformans* is melanized in pigeon excreta: implications for pathogenesis. *Infect. Immun.* 67(10):5477–79, 1999.
24. Nosanchuk et al., Melanization of *Cryptococcus neoformans* in murine infection. *Mol. Cell. Biol.*, 19:745–50, 1999.
25. Rosas et al., Synthesis of polymerized melanin by *Cryptococcus neoformans* in infected rodents. *Infect. Immun.* (in press), 2000.
26. Nosanchuk et al., Evidence of zoonotic transmission of *Cryptococcus neoformans* from a pet cockatoo to an immunocompromised patient. Ann. Intern. Med. 132(3): 205–08, 2000.
27. Smith and Oehme, The biological activity of glyphosate to plants and animals: a literature review. *Veterinary and Human Toxicology*, 34(6):531–43, 1992.
28. Franz et al., Glyphosate: a unique global herbicide (Washington, D.C.: American Chemical Society, 1997).
29. Steinrucken and Amrhein, The herbicide glyphosate is a potent inhibitor of 5-enolpyruvylshikimic acid-3-phosphate synthase. *Biochemical* and *Biophysical Research Communications*, 94(4):1207–1212, 1980.
30. Kishore and Shaw, Amino acid biosynthesis inhibitors as herbicides. *Annu. Rev. Biochem.*, 57:627–63, 1988.
31. Roberts et al., Evidence for the shikimate pathway in apicomplexan parasites. *Nature*, 393:801–05, 1998.
32. Gossbard, E., Effects of glyphosate on the microflora: with reference to the decompensation of treated vegetation and interaction with some plant pathogens. In *The Herbicide Glyphosate* (London: Butterworths, 1985) 159–85.
33. Wardle and Parkinson, Influence of the herbicide glyphosate on soil microbial community structure. *Plant and Soil*, 122:29–37, 1990.
34. Butler and Day, Fungal melanins: a review. *Can. J. Microbiol.*, 44:1115–36, 1998.

35. Beers and Berkow, eds., *The Merck Manual of Diagnosis and Therapy*, 17$^{th}$ ed. (Whitehouse Station, N.J.: Merck Research Laboratories, 1999) 1209–11; 1218–20.
36. Jones et al., Molecular cloning, characterization and analysis of the regulation of the ARO2 gene, encoding chorismate synthase, of *Saccharomyces cerevisiae*. *Molecular Microbiology*, 5 (9):2143–52, 1991.
37. Madsen et al., Stability constants of copper(II), zinc, manganese(II), calcium, and magnesium complexes of N-(phosphonomethyl)glycine (glyphosate). *Acta Chimica Scandinavica* A, 32:79–83, 1978.
38. Motekaitis and Martell, Metal chelate formation by N-phosphonomethylglycine and related ligands. *J. Coord. Chem.*, 14:139–49, 1985.
39. Okey et al., Predicting stability constants of various chelating agents using QSAR technology. In Pohland Ta, ed., *Emerging Technologies in Hazardous Waste Management* (New York: Plenium, 1997).
40. Robinson et al., Early mycological treatment failure in AIDS-associated cryptococcal meningitis. *Clinical Infectious Diseases*, 28:82–92, 1999.
41. Casadevall et al., Characterization of a murine monoclonal antibody to *Cryptococcus neoformans* polysaccharide that is a candidate for human therapeutic studies. *Antimicrobial Agents and Chemotherapy*, 42:1437–46, 1998.
42. Davies et al., (6S)-6-fluoroshikimic acid, an antibacterial agent acting on the aromatic biosynthetic pathway. *Antimicrobial Agents & Chemotherapy*, 38(2):403–06, 1994.
43. Marzabadi et al., An EPSP synthase inhibitor joining shikimate 3-phosphate with glyphosate: synthesis and ligand binding studies. *Biochemistry*, 35(13):4199–210, 1996.
44. Ikeda and Jacobson, Heterogeneity of phenol oxidases in *Cryptococcus neoformans. Infect. Immun.*, 60(9): 3552–55, 1992.
45. Stryer, L., *Biochemistry*, 4$^{th}$ ed. (New York: W. H. Freeman and Company, 1995) 724–726.
46. Gossbard, E., Effects of glyphosate on the microflora: with reference to the decompensation of treated vegetation and interaction with some plant pathogens. In *The Herbicide Glyphosate* (London: Butterworths, 1985) 159–85.
47. Franz et al., Glyphosate: a unique global herbicide (Washington, D.C.: American Chemical Society, 1997).

All publications mentioned hereinabove are hereby incorporated in their entirety. While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A method for treating a mammal infected with a mammalian pathogenic fungus which uses melanin in virulence, comprising administering to the subject an amount of glyphosate effective to treat the infection systemically.

2. The method of claim 1, wherein the mammal is infected with *Cryptococcus neoformans*.

3. The method of claim 2, wherein the mammal has acquired immune deficiency syndrome (AIDS).

4. The method of claim 1, wherein the glyphosate is administered intradermally, intramuscularly, intraperitoneally, intravenously, or subcutaneously.

5. The method of claim 4, wherein the glyphosate is administered intraperitoneally.

6. A method for inhibiting proliferation of a mammalian pathogenic fungus which uses melanin in virulence, comprising contacting the fungus with an amount of glyphosate effective to inhibit the proliferation of the fungus.

7. The method of claim 6, wherein the fungus is *Cryptococcus neoformans*.

8. A method for inhibiting melanogenesis in a microorganism which produces melanin, comprising contacting the microorganism with an amount of glyphosate effective to inhibit melanogenesis in the microorganism.

9. The method of claim 8, wherein the microorganism is *Cryptococcus neoformans*.

10. The method of claim 1, wherein the glyphosate is administered at a dose ranging from about 45 mg/kg to about 90 mg/kg.

* * * * *